(12) United States Patent
Hill (10) Patent No.: US 11,998,167 B2
(45) Date of Patent: Jun. 4, 2024

(54) REMOTE MEDICAL EXAMINATION

(71) Applicant: COHI GROUP LLC, Arden Hills, MN (US)

(72) Inventor: Courtney Hill, Arden Hills, MN (US)

(73) Assignee: COHI GROUP LLC, Arden Hills, MN (US)

( * ) Notice: Subject to any disclaimer, the term of this patent is extended or adjusted under 35 U.S.C. 154(b) by 290 days.

(21) Appl. No.: 17/450,133

(22) Filed: Oct. 6, 2021

(65) Prior Publication Data

US 2022/0104688 A1 Apr. 7, 2022

Related U.S. Application Data (60) Provisional application No. 63/087,924, filed on Oct. 6, 2020.

(51) Int. Cl.

| | |
|---|---|
| A61B 1/00 | (2006.01) |
| A61B 1/04 | (2006.01) |
| A61B 1/07 | (2006.01) |
| A61B 1/227 | (2006.01) |
| A61B 5/00 | (2006.01) |
| G06T 7/00 | (2017.01) |
| G16H 30/20 | (2018.01) |
| G16H 40/67 | (2018.01) |
| G16H 50/20 | (2018.01) |

(52) U.S. Cl.
CPC ...... *A61B 1/00016* (2013.01); *A61B 1/00105* (2013.01); *A61B 1/04* (2013.01); *A61B 1/07* (2013.01); *A61B 1/227* (2013.01); *A61B 5/6898* (2013.01); *A61B 5/7267* (2013.01); *A61B 5/7282* (2013.01); *G06T 7/0012* (2013.01); *G16H 30/20* (2018.01); *G16H 40/67* (2018.01); *G16H 50/20* (2018.01); *G06T 2207/20081* (2013.01); *G06T 2207/30004* (2013.01)

(58) Field of Classification Search
CPC ............................ A61B 1/00016; A61B 1/227
USPC .................................................. 600/184–245
See application file for complete search history.

(56) References Cited

U.S. PATENT DOCUMENTS

| | | | |
|---|---|---|---|
| 5,235,510 | A | 8/1993 | Yamada et al. |
| 8,630,867 | B2 | 1/2014 | Yoo |
| 8,858,430 | B2 | 10/2014 | Oyadiran et al. |
| 9,445,713 | B2 | 9/2016 | Douglas et al. |
| 9,830,423 | B2 | 11/2017 | Biswas et al. |
| 10,468,131 | B2 | 11/2019 | Macoviak et al. |
| 2012/0245422 | A1 | 9/2012 | Hasbun |

(Continued)

OTHER PUBLICATIONS

Agency for Healthcare Research and Quality, US Department of Health & Human Services. "Otitis Media With Effusion: Comparative Effectiveness of Treatments" (Mar. 20, 2012). Retrieved on Oct. 6, 2020 from www.effectivehealthcare.ahrq.gov.

(Continued)

*Primary Examiner* — Eduardo C Robert
*Assistant Examiner* — Tara Rose E Carter
(74) *Attorney, Agent, or Firm* — Fredrikson & Byron, P.A.

(57) ABSTRACT

A platform, tips, and otoscope systems are described herein that can aid with evaluation of human ears (specifically children's ears), diagnose middle ear disease, and suggest appropriate treatments. The platform can serve as an end-to-end evaluation, treatment, and delivery of treatment to a user without requiring an office visit, and improves the accuracy of such systems and ease-of-use.

20 Claims, 8 Drawing Sheets

(56) References Cited

U.S. PATENT DOCUMENTS

| | | | | |
|---|---|---|---|---|
| 2014/0073880 | A1* | 3/2014 | Boucher | G16H 30/20 600/109 |
| 2015/0065803 | A1* | 3/2015 | Douglas | G06T 7/143 600/200 |
| 2018/0000336 | A1* | 1/2018 | Gilad-Gilor | A61B 1/005 |
| 2019/0216308 | A1* | 7/2019 | Senaras | A61B 1/227 |

OTHER PUBLICATIONS

Alsarraf, Ramsey, et al. "Measuring the Indirect and Direct Costs of Acute Otitis Media." Arch Otolaryngol Head Neck Surg. (Jan. 1999), 125(1):12-18.

AMWELL (American Well Corporation). "Ear pain treatment online." Retrieved Oct. 6, 2020, from https://amwell.com/cm/conditions/ear-pain/.

Crowson, Matthew et al. "AutoAudio: Deep Learning for Automatic Audiogram Interpretation" [Preprint]. May 5, 2020. DOI:10.1101/2020.04.30.20086637.

Dedhia, K et al. "External Auditory Canal: Inferior, Posterior-Inferior, and Anterior Canal Wall Overhangs." Int J Pediatr Otorhinolaryngol. (Jun. 2018), 109:138-143.

Kaur, Ravinder, et al. "Epidemiology of Acute Otitis Media in the Postpneumococcal Conjugate Vaccine Era." Pediatrics (Sep. 2017), 140(3):e20170181.

Lounsbery, Kayla. "Editorial: Healthcare's primary decision-maker is female." NRC Health, Marketing, Market Insights, (Mar. 30, 2018). Retrieved on Oct. 6, 2020, from https://nrchealth.com/editorial-healthcares-primary-decision-maker-female/.

Myburgh, Hermanus C. et al. "Towards low cost automated smartphone—and cloud-based otitis media diagnosis." Biomedical Signal Processing and Control (Jan. 2018), 39:34-52.

Pichichero, Michael, et al. "Assessing Diagnostic Accuracy and Tympanocentesis Skills in the Management of Otitis Media." Arch Pediatr Adolesc Med. (2001), 155(10):1137-1142.

Shah, Manan Udayan, et al. "iPhone otoscopes: Currently available, but reliable for tele-otoscopy in the hands of parents?" International Journal of Pediatric Otorhinolaryngology (2018), 106: 59-63.

US Bureau of Labor Statistics. "Women in the labor force: a databook," BLS Reports (Dec. 2019). Retrieved on Oct. 6, 2020.

US Department of Labor Employee Benefits Security Administration. "General Facts on Women and Job Based Health." Retrieved on Oct. 6, 2020.

* cited by examiner

REMOTE MEDICAL EXAMINATION

PRIORITY CLAIM

The present application claims priority from U.S. Provisional Application No. 63/087,924, filed Oct. 6, 2020, which is hereby fully incorporated herein by reference.

TECHNICAL FIELD

The present disclosure relates to medical diagnostic equipment for use at home. In particular, described herein are a system, device, and method that relate to detection and analysis of a tympanic membrane.

BACKGROUND

The subject matter of this patent document relates to a telemedicine platform for evaluating ears, diagnosing lateral canal/tympanic membrane/middle ear images (e.g., ear infection, ear fluid, or normal), prescribing treatment, counseling on supportive care measures, and facilitating the delivery or delivering the treatment prescribed. The platform can provide a way for parents to care for their child's ear pain with accurate diagnosis and timely treatment and minimize indirect costs of care including missed work, transportation, and sunk childcare costs. The minimum indirect costs of care for an ear infection are estimated to be $625. The additional physical and emotional toll of caring for a child who loses sleep and is in pain cannot be quantified.

It is more likely that mothers, rather than fathers, care for an ill child. These mothers need a solution that allows them to care for their child outside of normal working hours. In 2018, 65% of women with children under age 6 participated in the workforce, an increase from 39% in 1975. Working moms, in particular, can benefit from 24/7 access to an immediate assessment of their child's ears with treatment prescribed or guidance given for care. Women would otherwise need to take at least a half day off from work for an evaluation of their child's ears by a healthcare provider. The alternative is a costly visit to the emergency room or urgent care during afterhours. On both a societal and individual level, the difficulties in balancing childcare with work responsibilities contribute to stifling advancements in the workplace; this disproportionately affects women. A solution is needed that addresses this imbalance that predominantly affects mothers.

A typical child's ear canal is tortuous. It is a hallway that ends at the tympanic membrane but has twists and turns that have been studied. Mean anterior canal angle is 148 degrees and the mean inferior canal angle is 146 degrees. Because of this, the user of an otoscope has to identify an optimal view of the TM by angling and moving the otoscope tip. It can be difficult for home healthcare providers (e.g., parents) to navigate this using a conventional straight otoscope tip and recognize the anatomical structures within view.

Children benefit from care that is not delayed and from which they receive a reliably accurate diagnosis. In contrast, the mean diagnostic accuracy for ear infections and middle ear fluid by pediatricians is about 50%. This results in an abundance of over diagnosis of ear infections and over prescribing antibiotics. Ear infections play a large part in the care required for young children; they are one of the most common reasons for children to seek care in the US.

Not only can children have reactions to medications that might not be warranted, but inappropriate use of antibiotics drives antibiotic resistance within society. Society can benefit from appropriate antibiotic use when the diagnosis is more accurate.

SUMMARY

In embodiments disclosed herein, a platform for ear infection detection in children that addresses the above-identified problems is discussed. The platform disclosed serves to evaluate children's ears at any time of the day to provide the parent with an accurate diagnosis and appropriate treatment, including prescription antibiotics or supportive care measures. Parents are prompted to photograph their child's ear drums with a smartphone otoscope attachment. An algorithm analyzes the images and potentially yields a diagnosis with accuracy superior to the mean accuracy for pediatricians and ENT surgeons, 50% and 73%, respectively. The algorithm provides artificial intelligence, and can be based on machine learning, deep learning, or a convolutional neural network, for example. The success of the platform hinges on its diagnostic accuracy, which necessitates that the inputs to the algorithm are labeled accurately. Since physicians cannot achieve 100% accuracy, simply labeling images by a physician will not achieve this. Instead, by linking an image to the surgical findings of what is directly visualized in the middle ear space at the time of myringotomy (hole in the ear drum made for ear tube placement), up to 100% accuracy of the inputs to train and test the algorithm can be achieved. Machine learning-enabled, home diagnostics for middle ear disease is novel, transformative, and disruptive. Current state of the art for at home diagnostics consists of healthcare providers struggling to see the ear drum through telemedicine or on-call providers prescribing antibiotics for a presumed infection without having examined the ear drum.

Success of a platform such as is disclosed herein hinges on its accuracy and its usability. Accurate outputs depend on accurate inputs. Accurate labeling of training images only occurs when the middle ear status is defined by findings when a myringotomy is made (incision in the ear drum) or when the middle ear space is aspirated with a needle through the ear drum. For example, this can be achieved by photographing the ear drum directly before an incision is made in it for placing ear tubes. Once the incision is made, the contents of the middle ear space will come through and are visible to the ENT surgeon. This allows for 100% accurate labeling of the image as being normal, having fluid, or having infection in the middle ear space. The presence of fluid is the definition of "otitis media with effusion" and the presence of infected fluid is the definition of "acute otitis media." The latter is treated with antibiotics while the former is not. It is believed that misdiagnosis of infection and over prescription of antibiotics is a significant contributor to antibiotic resistance within society.

According to an embodiment, a system is described that includes a web-based application consisting of software that, used in conjunction with angled otoscope tips, can evaluate human ears, diagnose middle ear disease, suggest appropriate treatment for the diagnosis, offer recommendations for supportive care, send in prescription to a pharmacy, and deliver the medication to the user's home, wherein the platform can serve as an end-to-end evaluation, treatment, and delivery of treatment to a user without leaving the locale that they interact with the platform.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION OF THE DRAWINGS

In general, described herein are apparatuses and methods for the visual detection of the tympanic membrane (TM) and diagnosis of the middle ear, specifically that of a child. These apparatuses and methods are configured for use by a non-healthcare professional, such as a parent or caregiver. One such system described herein comprises a camera, light, otoscope, otoscope tip, and web-based application. The otoscope may be an otoscope typically used in a clinical setting or a smartphone otoscope attachment. The camera and/or light may be part of the traditional otoscope or may be the smartphone camera and light. Various embodiments of the otoscope tip exist, including (but not limited to) those illustrated in FIGS. 1-6.

Figure 1:
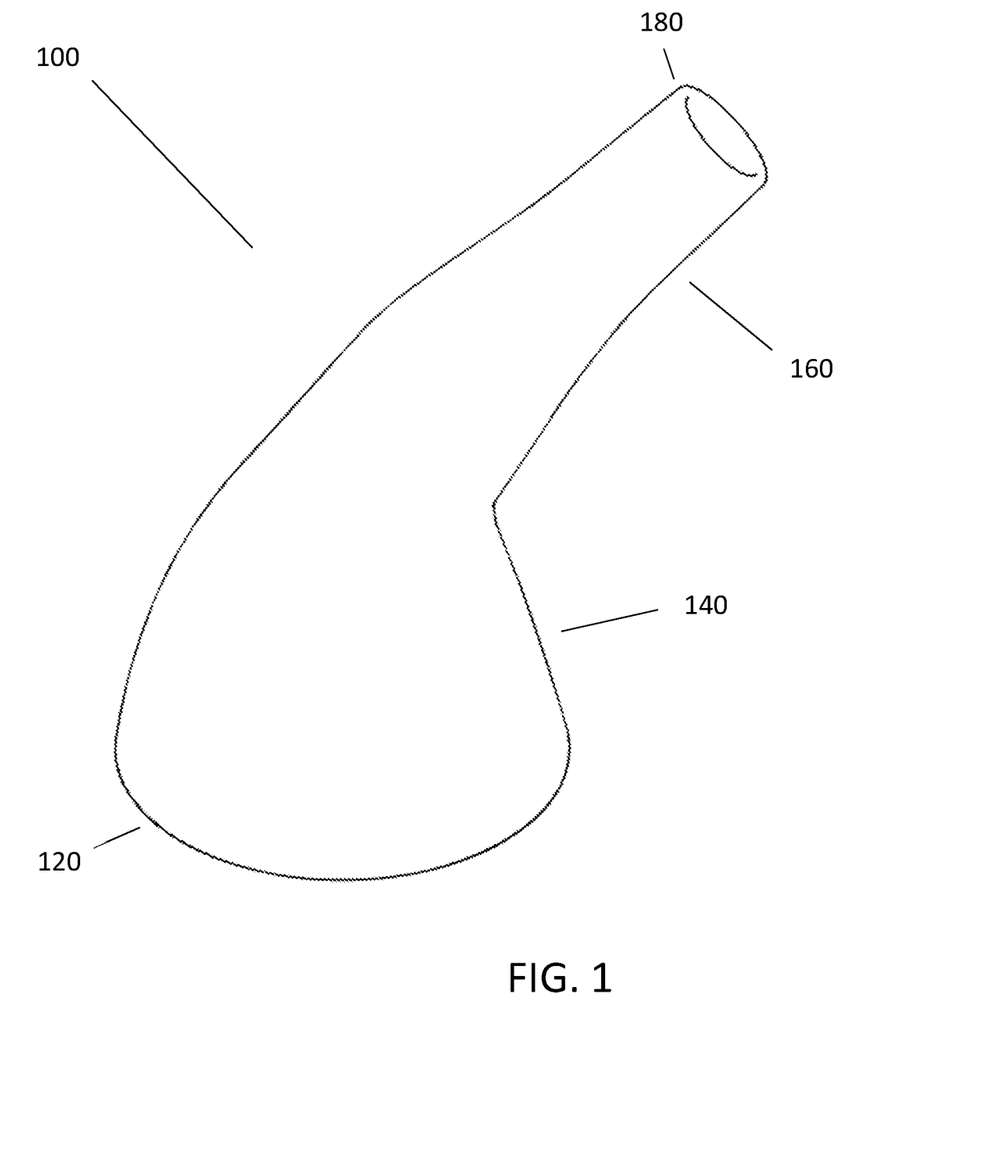
FIG. 1 is a perspective view of an otoscope tip, according to an embodiment.
Figure 2:
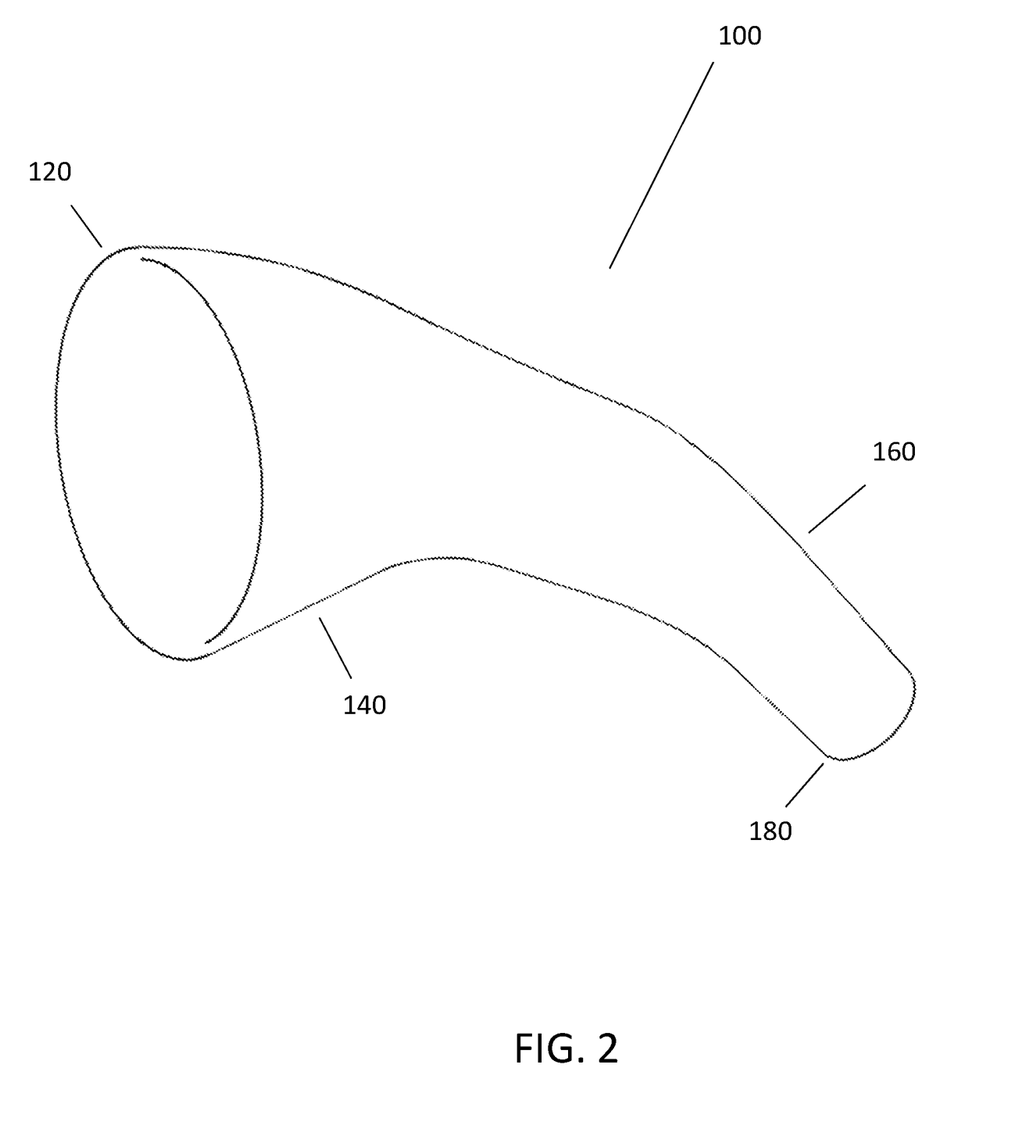
FIG. 2 is a perspective view of the otoscope tip, according to the embodiment depicted in FIG. 1.

One embodiment of otoscope tip 100 is shown in FIGS. 1 and 2. Otoscope tip 100 comprises a distal end 120, a substantially conical portion 140, a substantially cylindrical portion 160, and a proximal end 180. Throughout this application, "distal" and "proximal" are used to refer to the direction and distance relative to the patient. In use, the distal end 120 mounted onto the speculum of an otoscope. The user can insert the proximal end 180 into the ear and guides the cylindrical portion 160 along the ear canal.

In general, the most useful information for identifying an ear infection is "downward-and-forward facing" image capture. By "forward," this disclosure refers to photographs facing toward the face from the inside of the ear canal. By "downward," this disclosure refers to photographs facing towards the bottom of the patient's ear when the patient is upright/standing. Some specific examples of sizes and angles that can be used to obtain such images are described with respect to FIGS. 3-6. In general, though, the tips described herein remove the reliance on the user to obtain the view but rather allow the tip to guide and obtain the view in a fail-safe way. It should be understood that the features shown in FIGS. 1 and 2 could be sized and shaped to accomplish this result. Obtaining a forward and downward facing image of the medial ear canal maximizes the likelihood of capturing and image that contains the majority of the tympanic membrane. This is due to the anatomy of ear canals in children typically coursing forward and slightly down from the opening that is seen in the outer ear. In adolescents and adults, the forward facing is similar but the downward facing gaze into the ear canal is much less necessary. Young children have the highest rates of ear infections in the population. This tip can theoretically be used for both ears, just simply rotated 180 degrees. In that case, there would be markings on the base to instruct on use for each side. Having clear instructions on the tip improves usability and safety.

Additionally, the tips described herein at FIGS. 1-6 could have coatings or other features that help to eliminate or clear wax. Ear wax can obstruct views of the relevant portions of the ear that are indicative of infections or other conditions. A coating applied to the tips can improve the images obtained.

Figure 3:
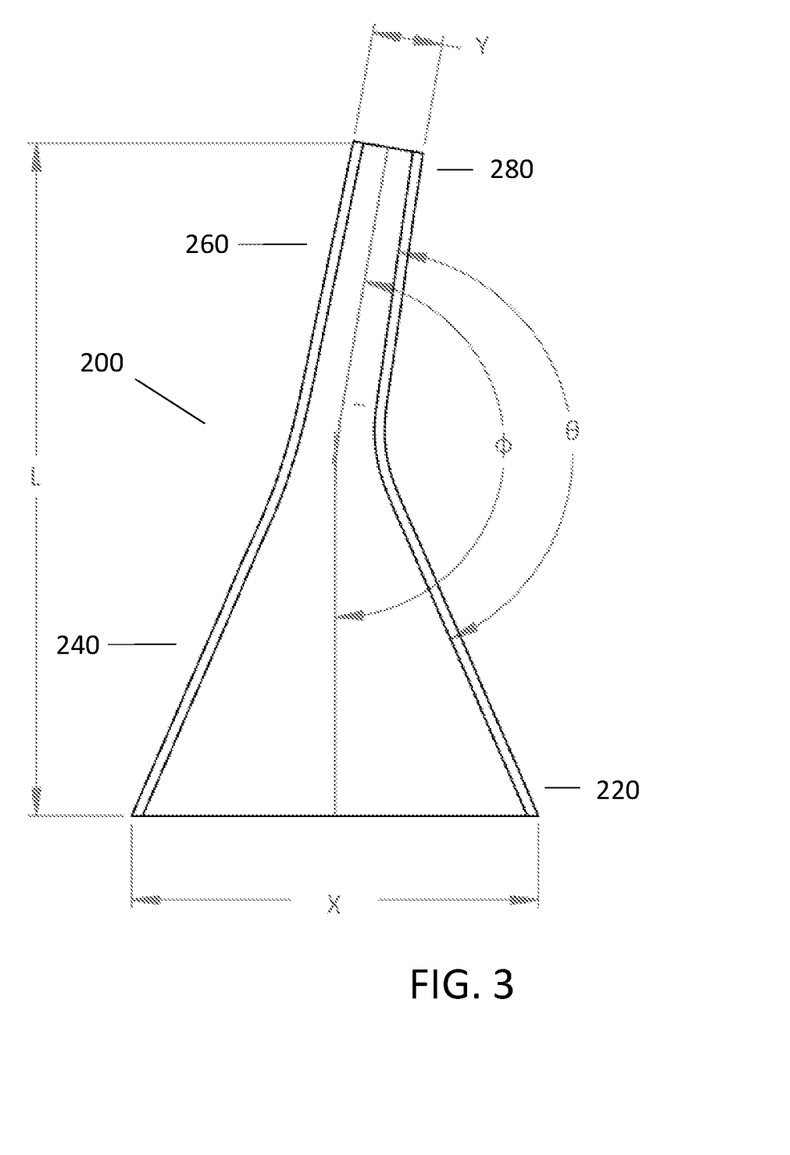
FIG. 3 is a cross-sectional side view of the otoscope tip, according to an embodiment.
Figure 4:
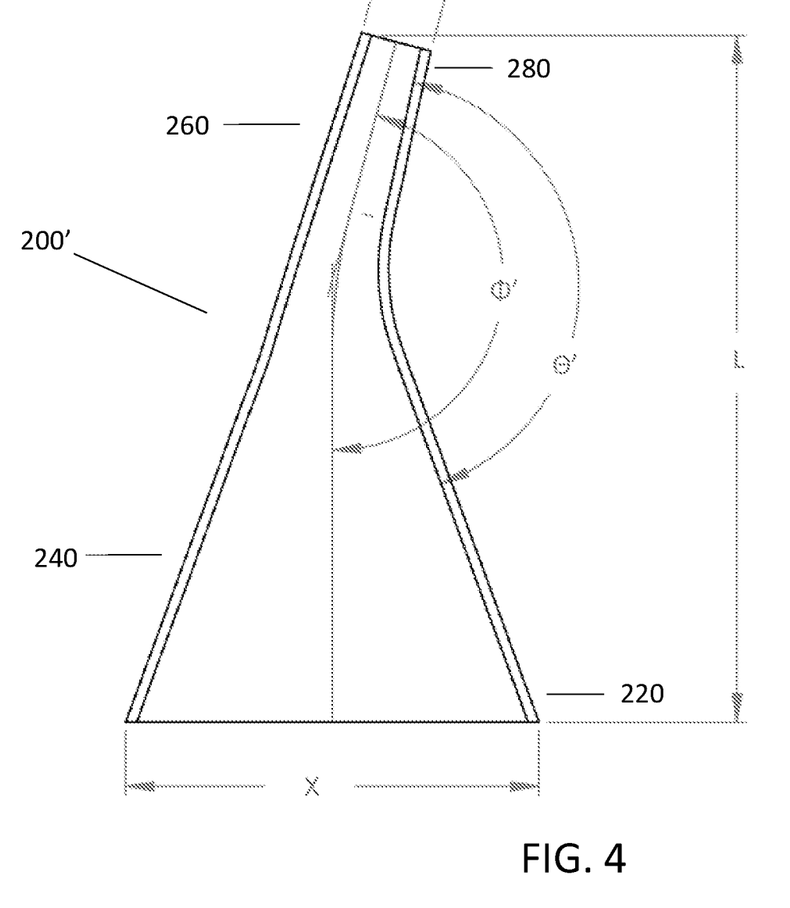
FIG. 4 is a cross-sectional side view of the otoscope tip, according to an embodiment.

In alternative embodiments illustrated in FIGS. 3 and 4, otoscope tip 200 is configured to solely accommodate the anterior angle of a child's ear canal. Throughout this application, like parts within different embodiments are described using like reference numbers, iterated by a multiple of 100. That is, similarly to the embodiments shown in FIGS. 1 and 2, otoscope tips 200 and 200' shown in FIGS. 3 and 4, respectively, each comprise a distal end 220, a substantially conical portion 240, a substantially cylindrical portion 260, and a proximal end 280. Otoscope tips 200 and 200' may have the same overall length L, distal end diameter X, and proximal end diameter Y. Otoscope tip 200', however, is configured for the ear canal of an older child. As a child grows, his or her ear canal lengthens. To reflect this lengthening, the location of the angle, between the conical portion 240 and the cylindrical portion 260, is farther from the distal end 220 in otoscope tip 200' than in otoscope tip 200. Therefore, the interior angles $\varphi$ and $\varphi'$ of otoscopes 200 and 200', respectively, are such that $\varphi > \varphi'$. In a particular embodiment, otoscope tips 200 and 200' may have overall length L=1.59 mm, distal end diameter X=0.956 mm, proximal end diameter Y=0.165 mm, anterior angles $\theta = \theta' = 148°$, interior angle $\varphi = 170°$, and interior angle $\varphi' = 165°$. It should be understood that these values are approximate and can vary over the age of the child, such that the anterior and inferior angles can become more shallow or less pronounced and the diameter of the canal increases.

Figure 5:
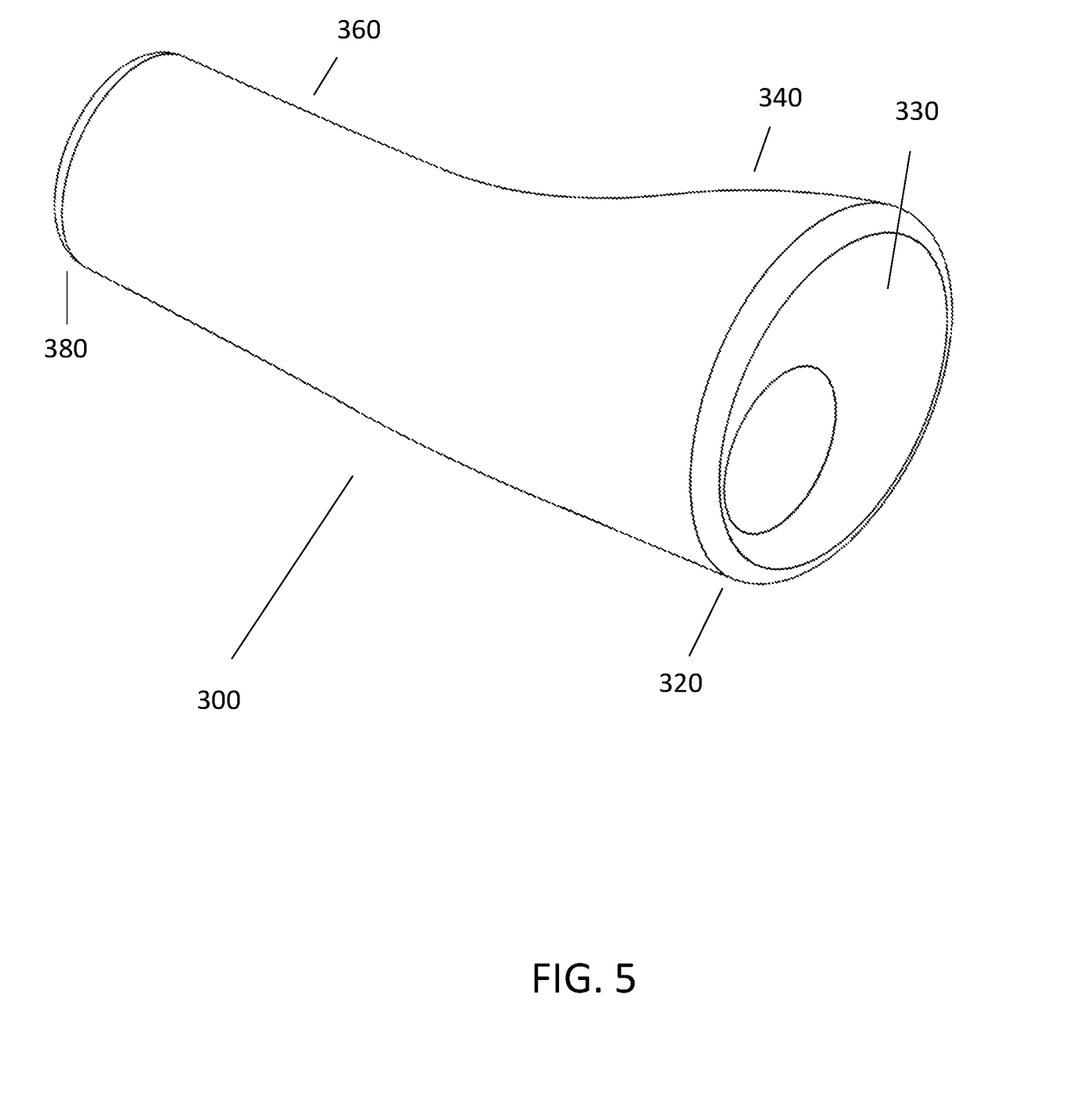
FIG. 5 is a perspective view of the otoscope tip, according to an embodiment.
Figure 6:
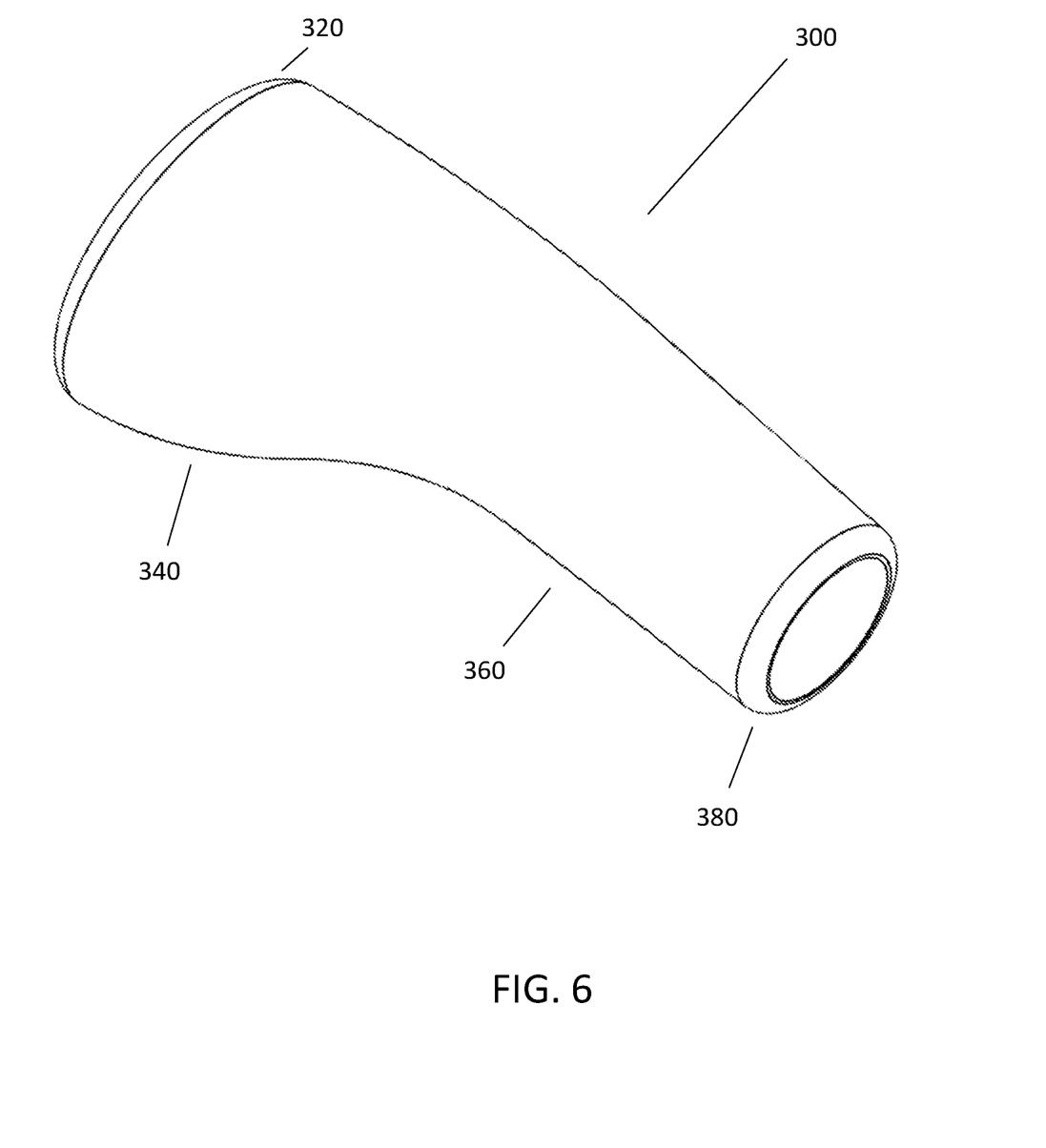
FIG. 6 is a perspective view of the otoscope tip, according to the embodiment depicted in FIG. 5.
Figure 7:
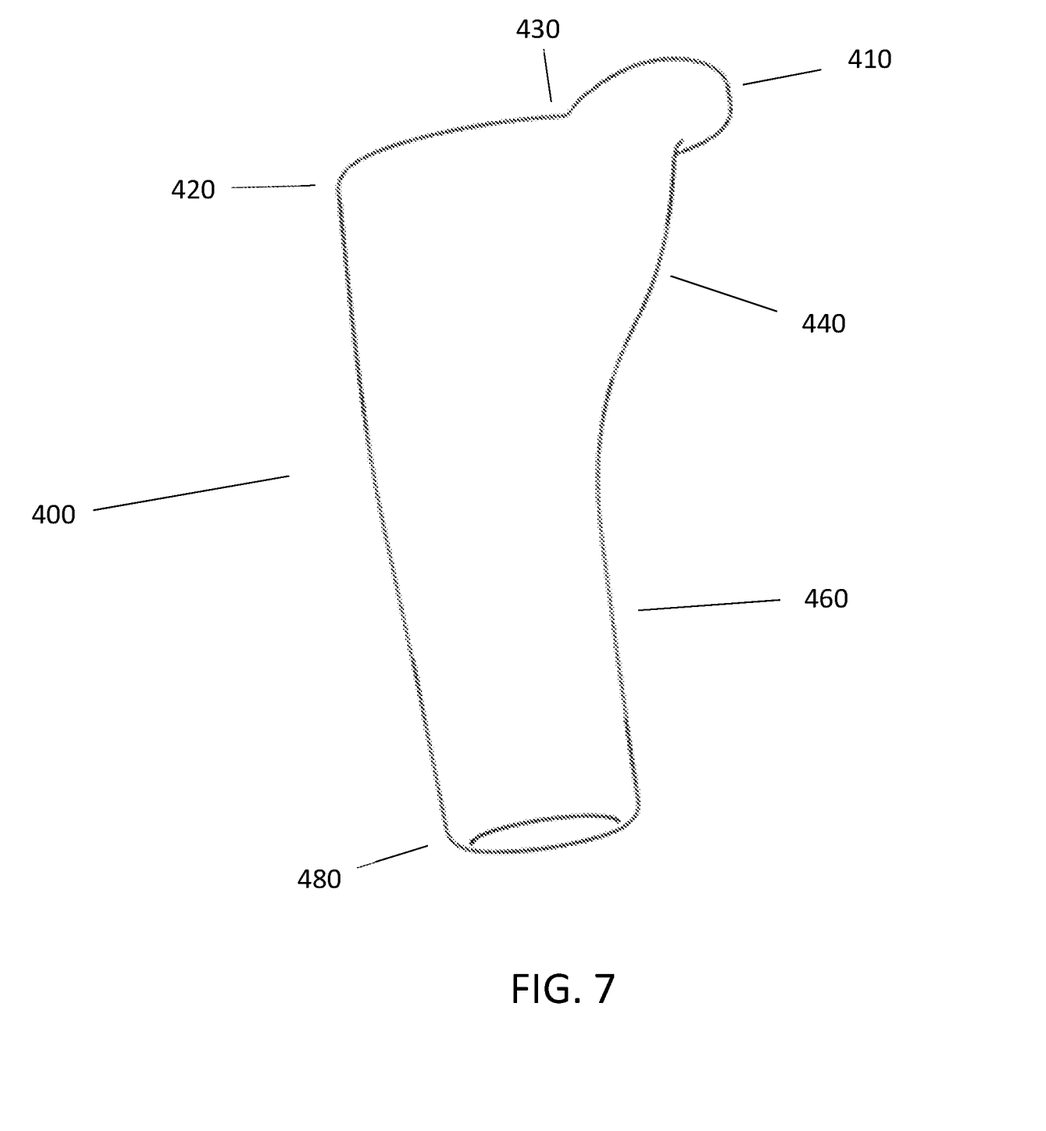
FIG. 7 is a perspective view of the otoscope tip, according to an embodiment.

Rather than bend around the anterior and inferior angles of the ear canal, alternative embodiments of the otoscope tip position the otoscope in optimal position, as shown in FIGS. 5-7. Similar to other embodiments, otoscope tip 300 comprises a distal end 320, a substantially conical portion 340, a substantially cylindrical portion 360, and a proximal end 380. In this embodiment, conical portion 340 further comprises an asymmetrically projecting extension 330. The extension 330 supports and suspends the otoscope in the ear, accommodating the angles of the ear canal without bending the trajectory of the light.

As shown in FIGS. 5 and 6, an embodiment is made to accommodate the anterior and inferior angles of a child's ear without necessarily bending around them but rather positioning the rigid otoscope in optimal position. When the otoscope is connected to the tip, its position starts posterior and superior at the base of the tip (end closer to the outside world) and ends anterior and inferior at the distal end of the tip (in the ear canal, end closer to the TM). In doing this, the otoscope is supported but suspended in the ear canal in a way that accommodates the angles of the child's ear canal. The length of the tip is meant to accommodate the length of the canal where the natural angles occur, and can be sized as described above with respect to FIGS. 1-4. In a kit embodiment, because the child's ears will spiral in the opposite way from one another, two separate tips (one for right ear and one for left ear) would be provided for use with an otoscope or camera.

An embodiment like that illustrated in FIGS. 5 and 6 is shown in FIG. 7. Otoscope tip 400 of FIG. 7 comprises a distal end 420, a substantially conical portion 440, a substantially cylindrical portion 460, and a proximal end 480. In this embodiment, the substantially conical portion 440 further comprises a flange 410 as well as an asymmetrically projecting extension 430. The flange 410 provides further support to the position of the otoscope within the ear and prevents it from falling or traveling too far into the ear canal. By controlling the depth of the otoscope tip 400, flange 410 improves alignment of the otoscope tip 400 with the ear canal and maintains focal distance for the camera, thereby increasing the success of image capture.

Otoscope tip 100 in FIGS. 1 and 2 is configured to accommodate a child's ear canal with respect to both the anterior angle, which as a mean angle of 148 degrees, and the inferior angle, which has a mean angle of 146 degrees. This geometric accommodation produces handedness and requires that two distinct tips be used, one for the left ear and one for the right ear. Two counterpart versions of otoscope tip 300 can be used for application to both ears. Unlike these embodiments, otoscope tip 200 and otoscope tip 200' may each be used for both ears if rotated 180 degrees.

Instructions referring to the body's anatomy or general spatial directions may be provided on the surface of the device to orient the appropriate position in the ear. Instructions may be written and/or pictorial. General spatial directions can include written words or symbols. There can be one or more sets of orienting images, symbols, or directions. Each set of orienting images, symbols, or directions can be color coded such that the color corresponds to instructions for one ear, and a separate color for the opposite ear. Providing instructions increases user ease and comfort as well as aids the success of auto-capture and visual classification.

Figure 8:
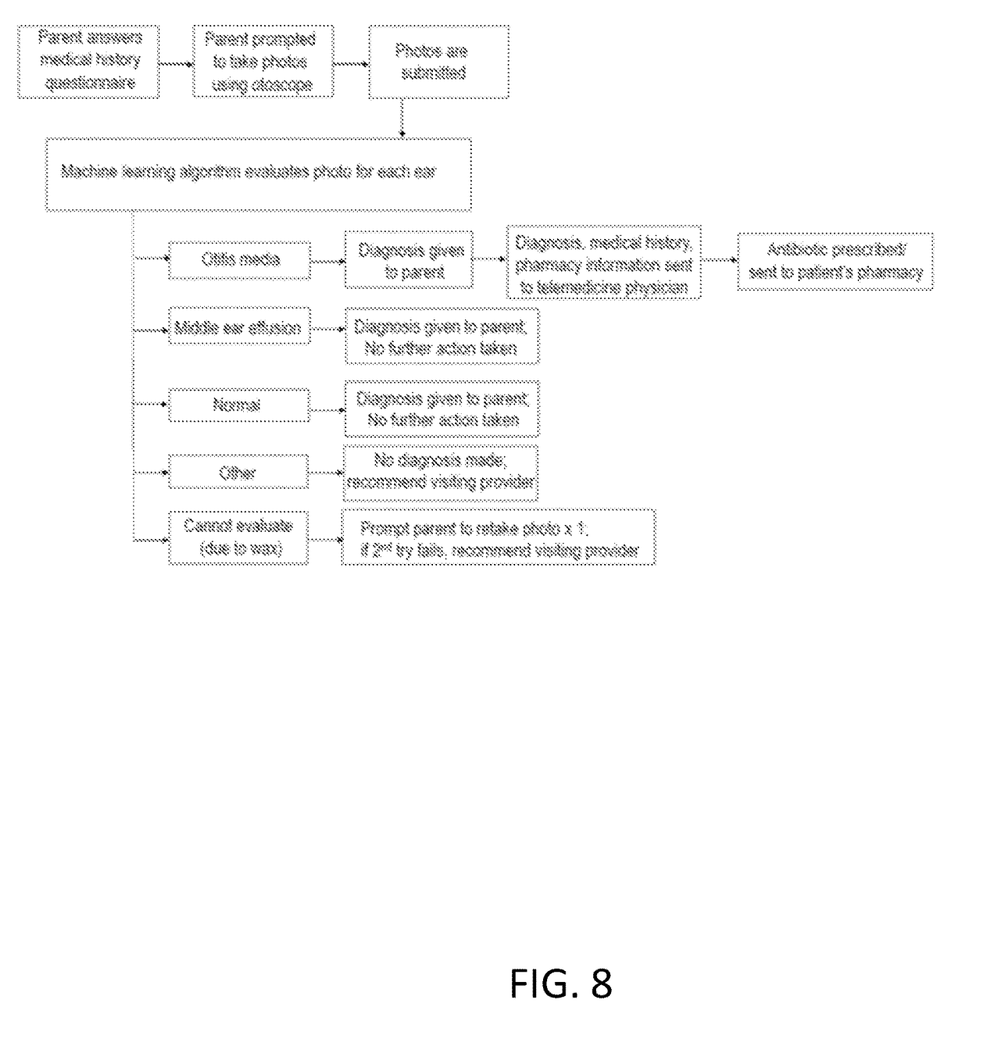
FIG. 8 is a flow diagram illustrating the user interaction with the platform.

Prior to using the otoscope, the parent (or other user) completes a medical history questionnaire, as indicated by the flow diagram in FIG. 8. The parent is then prompted to use the otoscope and otoscope tip system to take photos, which are then submitted to the web-based application. The application's software employs a machine learning algorithm to evaluate the photos. The platform disclosed serves to evaluate children's ears at any time of the day to provide the parent with an accurate diagnosis and appropriate treatment, including prescription antibiotics or supportive care measures. The platform disclosed can provide the parent with recommendations which include the need to seek care in person or via telemedicine or to continue supportive treatment at home. Parents are prompted to photograph their child's ear drums with a smartphone otoscope attachment. An algorithm analyzes the images and potentially yields a diagnosis with accuracy superior to the mean accuracy for pediatricians and ENT surgeons, 50% and 73%, respectively. The algorithm provides artificial intelligence, and can be based on machine learning, deep learning, or a convolutional neural network, for example. The success of the platform hinges on its diagnostic accuracy, which necessitates that the inputs to the algorithm are labeled accurately. Since physicians cannot achieve 100% accuracy, simply labeling images by a physician will not achieve this. Instead, by linking an image to the surgical findings of what is directly visualized in the middle ear space at the time of myringotomy (hole in the ear drum made for ear tube placement), up to 100% accuracy of the inputs to train and test the algorithm can be achieved.

Machine learning-enabled, home diagnostics for middle ear disease is novel, transformative, and disruptive. Current state of the art for at home diagnostics consists of healthcare providers struggling to see the ear drum through telemedicine or on-call providers prescribing antibiotics for a presumed infection without having examined the ear drum.

Success of a platform such as is disclosed herein hinges on its accuracy and its usability. Accurate outputs depend on accurate inputs. Accurate labeling of training images only occurs when the middle ear status is defined by findings when a myringotomy is made (incision in the ear drum) or when the middle ear space is aspirated with a needle through the ear drum. For example, this can be achieved by photographing the ear drum directly before an incision is made in it for placing ear tubes. Once the incision is made, the contents of the middle ear space will come through and are visible to the ENT surgeon. This allows for 100% accurate labeling of the image as being normal, having fluid, or having infection in the middle ear space. The presence of fluid is the definition of "otitis media with effusion" and the presence of infected fluid is the definition of "acute otitis media." The latter is treated with antibiotics while the former is not. It is believed that misdiagnosis of infection and over prescription of antibiotics is a significant contributor to antibiotic resistance within society.

The training images should include "real world" or high fidelity compared to what a parent can achieve at home in addition to images that physicians can achieve in the operating room or in the office. Manipulation of images to replicate various angles, out of focus, portions of ear drums (rather than entire ear drum), and images with wax partially obstructing the view of the ear drum are all ways that the training images can be used to help replicate real world images that parents can achieve at home. Multiple photographs can be taken of each ear drum to build the training image set. They can be taken before any ear wax is removed so that the native state of the ear canal can be captured. If no portion of the ear drum can be seen, then these images can be labeled as "cannot assess" so that when interacting with the platform, a child will be referred appropriately to their healthcare provider for an assessment rather than the algorithm attempting to label with a diagnosis. An image can be taken after the ear is cleaned to reveal the entire ear canal and ear drum. The images can also be taken with high definition surgical instruments such as endoscopic cameras or they can be taken with a commercially available smart phone otoscope attachment. The latter can provide an image quality similar to what parents could achieve in the home setting. If there is reasonable fidelity between future home images and the images that the algorithm is trained and tested with, the accuracy of the algorithm found in testing should translate to home use.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The invention claimed is:

1. A system for at-home imaging of a child's ear canal and diagnosis of middle ear disease, the system comprising:
 a light source configured to illuminate the ear canal;
 a camera configured to provide downward-and-forward facing images of the ear canal;
 an otoscope; and
 a web-based application configured to:
  receive the downward-and-forward facing images from the camera;
  output an insufficient image capture classification and a recommendation to consult with a healthcare provider when the received downward-and-forward facing images from the camera do not depict at least a portion of a tympanic membrane;
  autonomously capture the downward-and-forward facing images depicting at least a portion of the tympanic membrane; and
  autonomously classify the at least the portion of the tympanic membrane from the captured downward-and-forward facing images depicting the at least the portion of the tympanic membrane to indicate the status of the middle ear, the autonomous classification selected from a group consisting of: normal ear, middle ear fluid ("otitis media with effusion"), and middle ear infection ("acute otitis media").

2. The system of claim 1, wherein the camera is located within a smartphone otoscope attachment.

3. The system of claim 1, wherein the web-based application is further configured to:
 output a recommendation to consult with a healthcare provider when the received downward-and-forward facing images from the camera are autonomously classified as middle ear infection ("acute otitis media"); and
 output a recommendation for no further action needed or treating at-home when the received downward-and-forward facing images from the camera are autonomously classified as normal ear.

4. The system of claim 3, wherein the web-based application outputting the recommendation to consult with the healthcare provider when the received downward-and-forward facing images from the camera are autonomously classified as middle ear infection ("acute otitis media") comprises the web-based application outputting a middle ear infection ("acute otitis media") diagnosis to a telemedicine healthcare provider and a recommendation for an antibiotic prescription.

5. The system of claim 1, wherein the web-based application comprises a machine learning software component that has been trained with images of the same resolution as the camera.

6. The system of claim 5, wherein the software has been trained with images taken at a variety of angles and orientations.

7. The system of claim 5, wherein the software has been trained with images that include cerumen at least partially blocking the view of the tympanic membrane.

8. The system of claim 1, further comprising a coating applied to at least one otoscope tip, the coating configured to dissolve, displace, and repel obstructing cerumen.

9. The system of claim 1, further comprising at least one otoscope tip that can be used for both ears.

10. The system of claim 1, further comprising an otoscope tip configured for use with a left ear and an otoscope tip configured for use with a right ear.

11. The system of claim 1, further comprising a plurality of otoscope tips.

12. The system of claim 1, further comprising an otoscope tip that accommodates the mean angle of the anterior ear canal (148 degrees) and the mean angle of the inferior ear canal (146 degrees).

13. The system of claim 1, further comprising an otoscope tip that is configured to suspend the otoscope in the ear canal.

14. The system of claim 1, further comprising an otoscope the tip that is mountable onto the otoscope, the tip comprising:
 a distal end configured to receive the otoscope;
 a substantially conical portion that narrows as it extends from the distal end; and
 a substantially cylindrical portion extending from the substantially conical portion to a proximal end,
 wherein the otoscope tip comprises an optical pathway extending through the substantially conical portion and the substantially cylindrical portion,
 wherein an anterior angle formed between the substantially conical portion and the substantially cylindrical portion is between about 146 and about 148 degrees, and
 wherein an interior angle of the optical pathway between the substantially conical portion and the substantially cylindrical portion is between about 165 and about 170 degrees.

15. The otoscope tip of claim 14, further comprising a coating configured to dissolve cerumen.

16. The system of claim 1, wherein the web-based application is further configured to present a medical history questionnaire and receive answers to the medical history questionnaire pertaining to the status of the middle ear.

17. A system for at-home imaging of a child's ear canal and diagnosis of middle ear disease, the system comprising:
 a light source configured to illuminate the ear canal;
 a camera configured to provide downward-and-forward facing images of the ear canal; an otoscope; and
 a web-based application configured to:
  receive the downward-and-forward facing images from the camera;
  autonomously capture the downward-and-forward facing images depicting at least a portion of a tympanic membrane; and
  autonomously classify the at least portion of the tympanic membrane from the captured downward-and-forward facing images to indicate the status of the middle ear, wherein the web-based application comprises a machine learning software component that has been trained with images of the same resolution as the camera, and wherein the software has been trained with images that include a rim of an at-home otoscope tip.

18. A system comprising:
a light source configured to illuminate an ear canal;
a camera configured to provide downward-and-forward facing images of the ear canal;
an otoscope; and
a web-based application configured to:
  receive the downward-and-forward facing images from the camera;
  autonomously capture the downward-and-forward facing images depicting at least a portion of a tympanic membrane; and
  autonomously classify the at least portion of the tympanic membrane from the captured downward-and-forward facing images to indicate the status of the middle ear,
wherein the web-based application comprises a machine learning software component that has been trained at least in part with: (i) one or more images of a tympanic membrane prior to a myringotomy, and (ii) one or more post-myringotomy surgical findings.

19. The system of claim 18, wherein the one or more post-myringotomy surgical findings comprise direct visualization of at least a portion of the middle ear through an incision in the tympanic membrane, and wherein the machine learning software component has been trained at least in part with the one or more images of the tympanic membrane prior to a myringotomy and with the one or more post-myringotomy surgical findings from direct visualization of at least the portion of the middle ear through the incision in the tympanic membrane.

20. The system of claim 19, wherein the web-based application is further configured to:
  output an insufficient image capture classification and a recommendation to consult with a healthcare provider when the received downward-and-forward facing images from the camera do not depict at least a portion of a tympanic membrane;
  output a recommendation to consult with a healthcare provider when the received downward-and-forward facing images from the camera are autonomously classified as middle ear infection ("acute otitis media"); and
  output a recommendation, the recommendation selected from the group consisting of: no further action needed, treat at-home, and consult with a healthcare provider, when the received downward-and-forward facing images from the camera are autonomously classified as normal ear and middle ear fluid ("otitis media with effusion").

* * * * *